United States Patent [19]

Kung et al.

[11] Patent Number: 4,913,996
[45] Date of Patent: Apr. 3, 1990

[54] ELECTROPHOTOGRAPHIC ELEMENTS CONTAINING CERTAIN ANTHRAQUINONE DERIVATIVES AS ELECTRON-TRANSPORT AGENTS

[75] Inventors: Teh-Ming Kung, Rochester; William B. Vreeland, Webster; Ralph H. Young, Rochester, all of N.Y.

[73] Assignee: Eastman Kodak Company, Rochester, N.Y.

[21] Appl. No.: 287,949

[22] Filed: Dec. 21, 1988

[51] Int. Cl.$^4$ ............................................... G03G 5/10
[52] U.S. Cl. .................................... 430/59; 430/73
[58] Field of Search ................. 430/58, 72, 59, 73

[56] References Cited

U.S. PATENT DOCUMENTS

| | | | |
|---|---|---|---|
| 3,615,414 | 10/1971 | Light | 430/58 |
| 4,175,960 | 11/1979 | Berwick et al. | 430/58 |
| 4,474,865 | 10/1984 | Ong et al. | 430/58 |
| 4,514,481 | 4/1985 | Scozzafava et al. | 430/58 |
| 4,559,287 | 12/1985 | McAneney et al. | 430/59 |
| 4,578,220 | 3/1986 | Huenig et al. | 260/239 |
| 4,578,334 | 3/1986 | Borsenberger et al. | 430/59 |
| 4,606,861 | 8/1986 | Ong et al. | 260/351 |
| 4,609,602 | 9/1986 | Ong et al. | 430/58 |
| 4,666,802 | 5/1987 | Hung et al. | 430/58 |
| 4,701,396 | 10/1987 | Hung et al. | 430/58 |
| 4,719,163 | 1/1988 | Staudenmayer et al. | 430/58 |

FOREIGN PATENT DOCUMENTS 62-32465  2/1987  Japan .

*Primary Examiner*—John L. Goodrow
*Attorney, Agent, or Firm*—David F. Janci

[57] ABSTRACT

New electrophotographic elements contain electron-transport agents comprising certain chemical compounds, which are derivatives of certain substituted 9,10-anthraquinones in which the keto oxygens have been replaced by cyanoimino groups.

3 Claims, No Drawings

ELECTROPHOTOGRAPHIC ELEMENTS CONTAINING CERTAIN ANTHRAQUINONE DERIVATIVES AS ELECTRON-TRANSPORT AGENTS

FIELD OF THE INVENTION

This invention relates to electrophotographic elements containing electron-transport agents comprising certain chemical compounds, which are derivatives of 9,10-anthraquinone. The chemical compounds can be relatively efficiently and simply prepared; they have good solubility or dispersibility in organic solvents and polymeric binders; and they exhibit unexpectedly good electron-transport properties in the inventive electrophotographic elements.

BACKGROUND

In electrophotography an image comprising a pattern of electrostatic potential (also referred to as an electrostatic latent image), is formed on a surface of an electrophotographic element comprising at least an insulative photoconductive layer and an electrically conductive substrate. The electrostatic latent image is usually formed by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

In latent image formation the imagewise discharge is brought about by the radiation-induced creation of electron/hole pairs, which are generated by a material (often referred to as a charge-generation or photoconductive material) in the electrophotographic element in response to exposure to the imagewise actinic radiation. Depending upon the polarity of the initially uniform electrostatic potential and the type of materials included in the electrophotographic element, either the holes or the electrons that have been generated migrate toward the charged surface of the element in the exposed areas and thereby cause the imagewise discharge of the initial potential. What remains is a non-uniform potential constituting the electrostatic latent image.

Most electrophotographic elements currently in use are designed to be initially charged with a negative polarity. Such elements contain material which facilitates the migration of positive holes toward the negatively charged surface in imagewise exposed areas in order to cause imagewise discharge. Such material is often referred to as a hole-transport agent. In elements of that type a positively charged toner material is then used to develop the remaining imagewise unexposed portions of the negative polarity potential (i.e., the latent image) into a toner image. Because of the wide use of negatively charging elements, considerable numbers and types of positively charging toners have been fashioned and are available for use in electrographic developers. Conversely, relatively few high quality negatively charging toners are available.

However, for some applications of electrophotography it is more desirable to be able to develop the surface areas of the element that have been imagewise exposed to actinic radiation, rather than those that remain imagewise unexposed. For example, in laser printing of alphanumeric characters it is more desirable to be able to expose the relatively small percentage of surface area that will actually be developed to form visible alphanumeric toner images, rather than waste energy exposing the relatively large percentage of surface area that will constitute undeveloped background portions of the final image. In order to accomplish this while still employing widely available high quality positively charging toners, it is necessary to use an electrophotographic element that is designed to be positively charged. Thus, positive toner can then be used to develop the exposed surface areas (which will have relatively negative electrostatic potential after exposure and discharge, compared to the unexposed areas, where the initial positive potential will remain).

An electrophotographic element designed to be initially positively charged should, however, contain an adequate electron-transport agent (i.e., a material which adequately facilitates the migration of photogenerated electrons toward the positively charged insulative element surface). Unfortunately (and analogous to the situation with positive and negative toners), many materials having good hole-transport properties have been fashioned for use in electrophotographic elements, but relatively few materials are known to provide good electron-transport properties in electrophotographic elements.

A number of chemical compounds having electron-transport properties are described, for example, in U.S. Pat. Nos. 4,175,960; 4,514,481; 4,474,865; 4,559,287; 4,606,861; and 4,609,602 and in Japanese published patent application No. 62-32465. However, many prior art compounds have one or more drawbacks.

Some prior art electron-transport agents do not perform the electron-transporting function very well, especially under certain conditions or when included in certain types of electrophotographic elements. Also, some cause an undesirably high rate of discharge of the electrophotographic element before it is exposed to actinic radiation (often referred to as high dark decay).

Some prior art electron-transport compounds are not soluble or dispersible or have relatively limited solubility or dispersibility in coating solvents of choice or in some polymeric binders desired to be used in charge-transport layers, such that attempts to include sufficient amounts of such electron-transport agents in electrophotographic elements result in some crystallization of the electron-transport agents, which in turn causes problems such as undesirable levels of dark decay and such as unwanted scatter or absorption of actinic radiation intended to pass undisturbed through the charge-transport layer to a radiation-sensitive portion of the element.

Furthermore, some electron-transport agents appear to impart undesirably poor regeneration properties to electrophotographic elements desired to be reusable. Reusable elements are those that can be practically utilized through a plurality (preferably a large number) of cycles of uniform charging (i.e., formation of the initially uniform electrostatic potential), imagewise exposure to actinic radiation to form the electrostatic latent image, and erasure of remaining potential, without unacceptable changes in their performance. Undesirably poor regeneration properties are manifested as a progressive rise of the final potential (also referred to as the residual potential) to which the element can be driven by the erasure process, caused by a buildup of residual charge within the electrophotographic element over time as the element is exercised through its normal cycles of electrophotographic operation. This buildup of residual charge is not removed by normal methods of erasure during normal cycles of operation, such as by exposure to excess amounts of actinic radiation. The resulting unerasable residual potential can build up to a level (e.g., higher than 100 volts) such that the element can no longer be discharged to the intended degree (e.g., from an initial potential of 500 volts to an intended potential of 100 volts) in areas of maximum imagewise exposure during latent image formation. This results in image artifacts such as lower image density in areas of maximum imagewise exposure that are intended to produce maximum image density. In effect, the element has become no longer reusable.

Also, some electron-transport agents suffer from being obtainable only through difficult, lengthy, and/or otherwise relatively inefficient or uneconomical methods of preparation.

Thus, there is a need for electrophotographic elements containing chemical compounds that exhibit good electron-transport properties in the elements without imparting undesirably poor regeneration or dark decay properties thereto. The electron-transport agents incorporated in the elements should be sufficiently soluble or dispersible in coating solvents and polymeric binders of choice, and should be capable of being readily prepared by relatively simple and efficient methods.

SUMMARY OF THE INVENTION

The present invention meets the above-noted need by providing new electrophotographic elements containing electron-transport agents comprising chemical compounds, which are derivatives of anthraquinone, having the structure

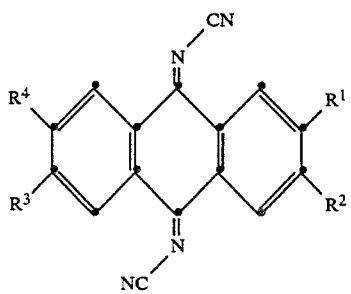

wherein:
one of $R^1$, $R^2$, $R^3$, and $R^4$ is acrylic alkyl having 2 to 10 carbon atoms or $-COOR^5$;
another one of $R^1$, $R^2$, $R^3$, and $R^4$ is H, acyclic alkyl having 1 to 10 carbon atoms, or $-COOR^5$;
the remaining two of $R^1$, $R^2$, $R^3$, and $R^4$ are each H; and $R^5$ is alkyl having 1 to 10 carbon atoms.

The chemical compounds of use as electron-transport agents in elements of the invention can be readily prepared by relatively simple and efficient methods. They have good solubility or dispersibility in many coating solvents and in many film-forming polymeric binders that are useful to form one or more layers in the inventive electrophotographic elements. In the inventive electrophotographic elements, the chemical compounds serve as electron-transport agents with good capability of accepting and transporting electrons generated by radiation-activated charge-generation materials in the elements, and they do not impart unacceptably high dark decay or undesirably poor regeneration properties to the elements.

It should be noted that other chemical compounds having good electron-transport capabilities, and also other inventive electrophotographic elements, different from those of the present invention, but devised to serve similar purposes, are described in copending U.S. patent application Ser. Nos. 287,946; 287,947; 287,948; and 287,950, all filed Dec. 21, 1988.

DESCRIPTION OF PREFERRED EMBODIMENTS

The chemical compounds of Structure (I) utilized as electron-transport agents in electrophotographic elements of the invention can be conveniently and efficiently prepared from readily available starting materials, for example, by combining an anthraquinone having the previously described appropriate $R^1$, $R^2$, $R^3$, and $R^4$ substituents with 2–3 equivalents of bistrimethylsilylcarbodiimide in an inert organic solvent in the presence of a catalyst. Examples of suitable solvents are dichloromethane, acetonitrile, trichloroethane, and dichloroethane. An example of a suitable catalyst is cesium fluoride.

When the appropriately R-substituted anthraquinone is not readily commercially available, it can be easily prepared by known methods from readily available materials. For example, 2-n-hexoxycarbonylanthraquinone can be prepared from 2-carboxyanthraquinone, by reaction with oxalyl chloride to form 2-chlorocarbonylanthraquinone, followed by reaction with 1-hexanol; and 2-t-butyl-6-methylanthraquinone can be prepared by reaction of 3-methylphthalic anhydride with t-butylbenzene in the presence of aluminum chloride, followed by reaction with thionyl chloride, and then ring closure in the presence of aluminum chloride.

Some specific examples of Structure (I) compounds that have been simply and efficiently prepared and have the advantageous properties previously noted, when included as electron-transport agents in electrophotographic elements of the invention, are those wherein:
$R^1$ is t-butyl, and $R^2$, $R^3$, and $R^4$ are each H;
$R^1$ is ethyl, and $R^2$, $R^3$, and $R^4$ are each H;
$R^1$ is hexoxycarbonyl, and $R^2$, $R^3$, and $R^4$ are each H;
$R^1$ is 2-ethylhexoxycarbonyl, and $R^2$, $R^3$, and $R^4$ are each H; and
$R^1$ is t-butyl, $R^3$ is methyl, and $R^2$ and $R^4$ are each H.

Some specific examples of compounds outside the scope of Structure (I) that are not useful in the present invention, because attempts to prepare them failed, are those wherein (referring to Structure (I) for convenience):

$R^1$, $R^2$, and $R^3$ are each methyl, and $R^4$ is H;
$R^1$ is $-O-(CH_2O)_4-CH_3$, and $R^2$, $R^3$, and $R^4$ are each H;
$R^1$ is $-SO_2-N(alkyl)_2$, and $R^2$, $R^3$, and $R^4$ are each H;
$R^1$ is cyclohexyl, and $R^2$, $R^3$, and $R^4$ are each H; and also compounds having the structures:

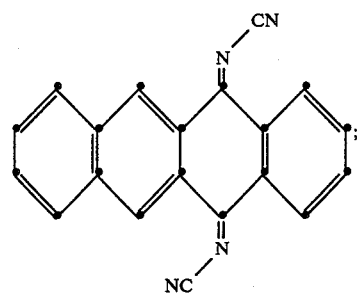

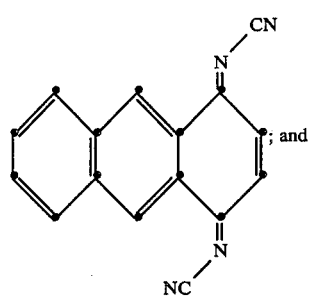

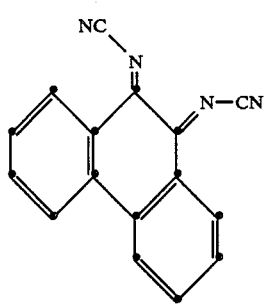

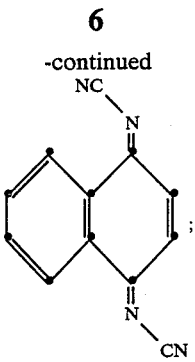

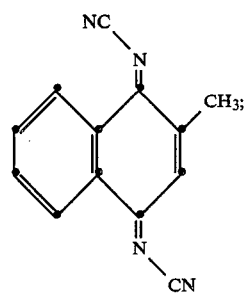

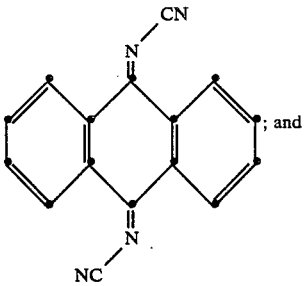

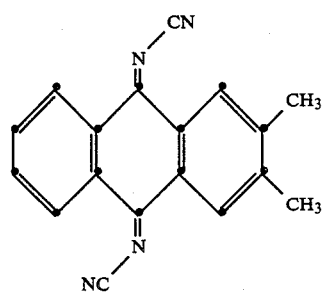

Some specific examples of compounds outside the scope of Structure (I) that are not useful in the present invention, because they could not be incorporated in electrophotographic elements in sufficient amounts in a non-crystalline state, because they were too insoluble in commonly used coating solvents (e.g., in tetrahydrofuran, dichloromethane, acetone, acetonitrile, toluene, and/or lower alcohols) and/or were too insoluble in or incompatible with polymeric binders commonly employed in charge-transport layers of electrophotographic elements (e.g., polycarbonates, polyesters, polystyrenes, and/or copolymers of styrenes and acrylates) are those having the structures:

Some specific examples of compounds outside the scope of Structure (I) that do not appear to be useful in the present invention, because they were unstable over time and caused high dark decay when it was attempted to utilize them as electron-transport agents in electrophotographic elements, are those having the strutures:

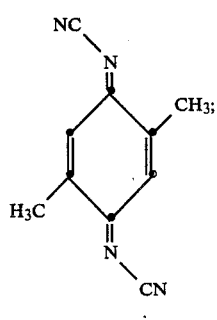

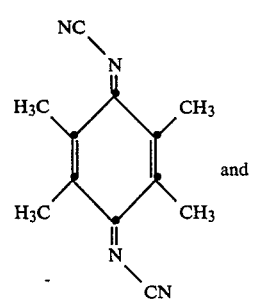

-continued

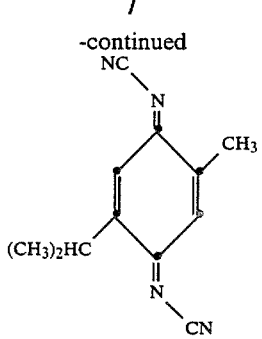

Some specific examples of compounds outside the scope of Structure (I) that are not useful in the present invention, because they imparted undesirably poor regeneration properties to electrophotographic elements when included therein as electron-transport agents (i.e., caused a high buildup of unerasable residual potential in the elements during repeated use) are those having the structures:

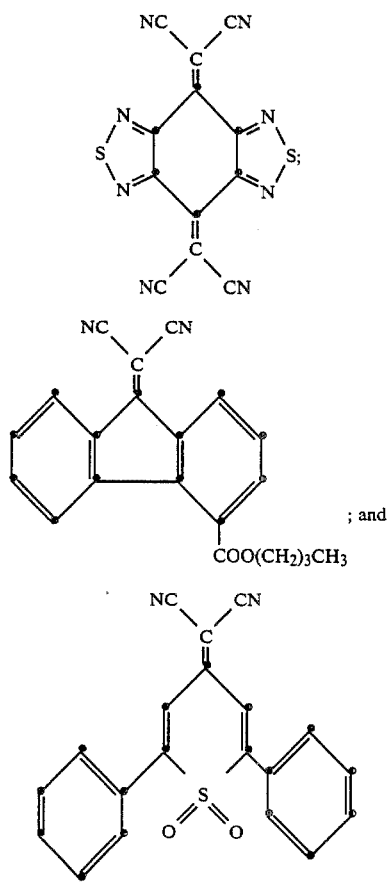

The new electrophotographic elements of the invention can be of various types, all of which contain one or more of the chemical compounds of Structure (I) described above to serve as electron-transport agents in the elements. The various types of inventive elements include both those commonly referred to as single layer or single-active-layer elements and those commonly referred to as multiactive, multilayer, or multi-active-layer elements.

Single layer elements are so named, because they contain only one layer that is active both to generate and to transport charges in response to exposure to actinic radiation. Such elements typically comprise at least an electrically conductive layer in electrical contact with a photoconductive layer. In single layer elements of the invention, the photoconductive layer contains a charge-generation material to generate electron/hole pairs in response to actinic radiation and an electron-transport material, comprising one or more of the chemical compounds of Structure (I) described above, which is capable of accepting electrons generated by the charge-generation material and transporting them through the layer to effect discharge of the initially uniform electrostatic potential. The photoconductive layer is electrically insulative, except when exposed to actinic radiation, and sometimes contains an electrically insulative polymeric film-forming binder, which may itself be the charge-generating material or may be an additional material which is not photoconductive. In either case the electron-transport agent is dissolved or dispersed as uniformly as possible in the binder film.

Multiactive elements are so named, because they contain at least two active layers, at least one of which is capable of generating charge in response to exposure to actinic radiation and is referred to as a charge-generation layer (hereinafter also referred to as a CGL), and at least one of which is capable of accepting and transporting charges generated by the charge-generation layer and is referred to as a charge-transport layer (hereinafter also referred to as a CTL). Such elements typically comprise at least an electrically conductive layer, a CGL, and a CTL. Either the CGL or the CTL is in electrical contact with both the electrically conductive layer and the remaining CGL or CTL. Of course, the CGL contains at least a charge-generation material (a photoconductor); the CTL contains at least a charge-transport agent; and either or both layers can contain an additional film-forming polymeric binder. In multiactive elements of the invention the charge-transport agent is an electron-transport agent comprising one of the chemical compounds of Structure (I) described above.

Single layer and multilayer electrophotographic elements and their preparation and use, in general, are well known and are described in more detail, for example, in U.S. Pat. Nos. 4,701,396; 4,666,802; 4,578,334; 4,719,163; 4,175,960; 4,514,481; and 3,615,414, the disclosures of which are hereby incorporated herein by reference. The only essential difference of electrophotographic elements of the present invention from generally known elements is that the new elements contain chemical compounds of Structure (I) as electron-transport agents.

In preparing single-active-layer electrophotographic elements of the invention, the components of the photoconductive layer, including any desired addenda, can be dissolved or dispersed together in a liquid and can be coated on an electrically conductive layer or support. The liquid is then allowed or caused to evaporate from the mixture to form the permanent layer containing from about 10 to about 70 percent (by weight) of the electron-transport agent and from about 0.01 to about 50 weight percent of the charge-generating material. Included among many useful liquids for this purpose are, for example, aromatic hydrocarbons such as benzene, toluene, xylene and mesitylene; ketones such as acetone and butanone; halogenated hydrocarbons such as methylene chloride, chloroform and ethylene chloride; ethers, including ethyl ether and cyclic ethers such as tetrahydrofuran; and mixtures thereof.

In preparing multiactive electrophotographic elements of the invention, the components of the CTL can similarly be dissolved or dispersed in such a liquid coating vehicle and can be coated on either an electrically conductive layer or support or on a CGL previously similarly coated or otherwise formed on the conductive layer or support. In the former case a CGL is thereafter coated or otherwise formed (e.g., by vacuum-deposition) on the CTL. The CTL will usually contain from about 10 to about 70 weight percent of the electron-transport agent, although concentrations outside that range may be found to be useful in some cases.

Various electrically conductive layers or supports can be employed in electrophotographic elements of the invention, such as, for example, paper (at a relative humidity above 20 percent); aluminum-paper laminates; metal foils such as aluminum foil, zinc foil, etc.; metal plates such as aluminum, copper, zinc, brass and galvanized plates; vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum-deposited on transparent film supports in sufficiently thin layers to allow electrophotographic elements prepared therewith to be exposed from either side.

Any charge-generation material can be utilized in elements of the invention. Such materials include inorganic and organic (including monomeric, metalloorganic and polymeric organic) photoconductors, for example, zinc oxide, lead oxide, selenium, phthalocyanine, perylene, arylamine, polyarylalkane, and polycarbazole materials, among many others.

When solvent-coating a photoconductive layer of a single-active-layer element or a CGL and/or CTL of a multiactive element of the invention, a film-forming polymeric binder can be employed. The binder may, if it is electrically insulating, help to provide the element with electrically insulating characteristics. It also is useful in coating the layer, in adhering the layer to an adjacent layer, and when it is a top layer, in providing a smooth, easy to clean, wear-resistant surface.

The optimum ratio of charge-generation or charge-transport material to binder may vary widely depending on the particular materials employed. In general, useful results are obtained when the amount of active charge-generation and/or charge-transport material contained within the layer is within the range of from about 0.01 to about 90 weight percent, based on the dry weight of the layer.

Representative materials which can be employed as binders in charge-generation and charge-transport layers are film-forming polymers having a fairly high dielectric strength and good electrically insulating properties. Such binders include, for example, styrene-butadiene copolymers; vinyl toluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly(methylstyrene); isobutylene polymers; polyesters, such as poly[ethylene-co-alkylenebis(alkyleneoxyaryl)phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloacrylates and vinyl acetate such as poly(vinyl-m-bromobenzoate-co-vinyl acetate); chlorinated poly(olefins), such as chlorinated poly(ethylene); and polyimides, such as poly[1,1,3-trimethyl-3-(4'-phenyl)-5-indane pyromellitimide].

Binder polymers should provide little or no interference with the generation or transport of charges in the layer. Examples of binder polymers which are especially useful include bisphenol A polycarbonates and polyesters such as poly[4,4'-(2-norbornylidene)diphenylene terephthalate-co-azelate].

CGL's and CTL's in elements of the invention can also optionally contain other addenda such as leveling agents, surfactants, plasticizers, sensitizers, contrast-control agents, and release agents, as is well known in the art.

Also, elements of the invention can contain any of the optional additional layers known to be useful in electrophotographic elements in general, such as, e.g., subbing layers, overcoat layers, barrier layers, and screening layers.

The following preparations and examples are presented to further illustrate some specific electrophotographic elements of the invention and chemical compounds useful as electron-transport agents therein.

Preparation A

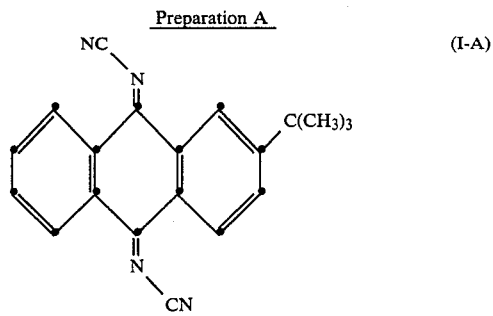

(I-A)

The compound of Structure (I-A) was prepared as follows.

To a magnetically stirred single neck 500 ml round bottom flask, containing a solution of 5.0 g (0.019 mole) 2-t-butyl-9,10-anthraquinone obtained from Aldrich Chemical Co., USA and 7.76 g (0.042 mole) bistrimethylsilylcarbodiimide obtained from Petrarch Chemical Co., USA, [structure: $(CH_3)_3Si-N=C=N-Si(CH_3)_3$] in 75 ml acetonitrile, was added a catalytic amount of cesium fluoride. Stirring was continued for 24 hours under an argon atmosphere. A precipitate of the compound of Structure (I-A) formed and was collected by filtration and washed with 25 ml cold acetonitrile. The crude yield was 70%. 4.16 g of the crude product was purified by filtration and recrystallization from 50 ml acetonitrile. 3.6 g of the Structure (I-A) compound was collected by filtration. Its structure was confirmed by infrared (IR) and nuclear magnetic resonance (NMR) spectroscopy.

Melting point=182°–184° C.

Elemental analysis: calculated for $C_{20}H_{16}N_4$: 17.9% N, 76.9% C, 5.2% H; found: 17.7% N, 76.7% C, 5.3% H.

Preparation B

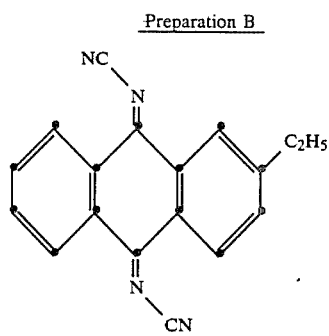

The compound of Structure (I-B) was prepared in a manner similar to Preparation A, except that the starting material was 2-ethyl-9,10-anthraquinone obtained from Aldrich Chemical Co., USA, and 2.5 equivalents of titanium tetrachloride reagent were employed instead of the cesium fluoride catalyst. The yield of Structure (I-B) compound was 85%. Its structure was confirmed by IR and NMR spectroscopy.

Melting point=147°–149° C.

Elemental analysis: calculated for $C_{18}H_{12}N_4$: 19.71% N, 76.04% C, 4.25% H; found: 19.68% N, 76.14% C, 4.05% H.

Preparation C

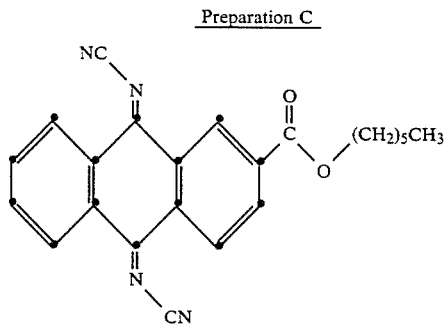

The compound of Structure (I-C) was prepared as follows. 2-carboxyanthraquinone was reacted with oxalyl chloride in dichloromethane (catalyzed by dimethylformamide) to yield 2-chlorocarbonylanthraquinone, which was then reacted with 1-hexanol in tetrahydrofuran (in the presence of triethylamine) to yield 2-n-hexoxycarbonylanthraquinone, which was then treated in a manner similar to Preparation A to prepare the Structure (I-C) compound with a yield of 50%. Structure was confirmed by IR and NMR spectroscopy.

Glass transition temperature=68°–110° C.

Elemental analysis: calculated for $C_{23}H_{20}N_4O_2$: 14.6% N, 71.9% C, 5.2% H; found: 14.7% N, 71.5% C, 5.2% H.

Preparation D

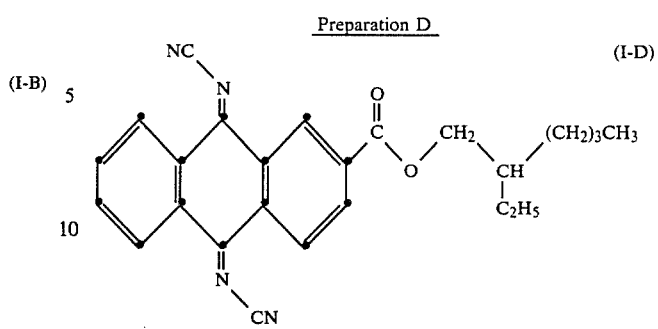

The compound of Structure (I-D) was prepared in a manner similar to Preparation C with a yield of 45%. Structure (I-D) was confirmed by IR and NMR spectroscopy.

Melting point=72°–74° C.

Elemental analysis: calculated for $C_{25}H_{24}N_4O_2$; 13.6% N, 72.8% C, 5.9% H; found: 13.9% N, 72.8% C, 5.8% H.

Preparation E

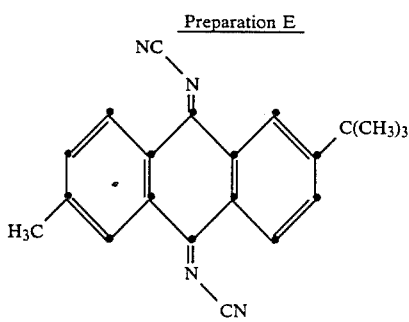

The compound of Structure (I-E) was prepared as follows. 3-Methylphthalic acid anhydride was reacted with t-butylbenzene in dichloromethane in the presence of aluminum chloride to yield 3-carboxyl-4-(4-t-butylphenylcarbonyl)toluene, which was reacted with thionyl chloride to yield 3-chlorocarbonyl-4-(4-t-butylphenylcarbonyl)toluene, which was then subjected to condensation ring closure in dichloromethane catalyzed by aluminum chloride to yield 2-t-butyl-6-methyl-9,10-anthraquinone, which was then treated in a manner similar to Preparation A (except that a stoichiometric amount of titanium tetrachloride reagent was employed instead of the cesium fluoride catalyst) to prepare the Structure (I-E) compound with a yield of 50%. Structure was confirmed by IR and NMR spectroscopy.

Melting point=152°–155° C.

Elemental analysis: calculated for $C_{21}H_{18}N_4$: 17.16% N, 77.28% C, 5.56% H; found: 16.84% N, 76.30% C, 5.46% H.

In the following Examples, the structure, preparation, and performance of various electrophotographic elements within the scope of the present invention are illustrated. In some of the Examples performance is illustrated in regard to electrophotographic speed (also referred to as sensitivity), dark decay properties, and regeneration characteristics.

In illustrating electrophotographic speed in the Examples, the element is electrostatically corona-charged to an initial positive potential (usually about 500 volts) and then exposed to actinic radiation (radiation having peak intensity at a wavelength to which the charge-generation material in the element is sensitive in order to generate electron/hole pairs) in an amount sufficient to photoconductively discharge a certain percentage of the initial voltage (usually 50% or 80% of the initial voltage). Electrophotographic speed is measured in terms of the amount of incident actinic radiant energy (expressed in ergs/cm$^2$) needed to achieve the desired percentage of discharge of the initial voltage. The lower the amount of radiation needed to achieve the desired degree of discharge, the higher is the electrophotographic speed of the element, and vice versa.

In illustrating dark decay properties in the Examples, the rate of dissipation of the initial voltage (expressed in V/s, i.e., volts per second) is measured while the element remains in darkness (i.e., before any exposure to actinic radiation). This is accomplished by measuring the initial voltage and the voltage remaining on the element after 2 seconds in darkness and dividing the difference by 2. The lower the rate of discharge in darkness, the better is the dark decay property of the element, i.e., the better is the element's ability to retain its initial potential before exposure.

In illustrating regeneration characteristics in the Examples, the electrophotographic element is subjected to a plurality of cycles of operation, with each cycle comprising initially uniformly charging the element, exposing the element to actinic radiation in an amount sufficient (in the first cycle) to photoconductively discharge 80 to 90% of the initial potential (to simulate imaging exposure), and then exposing the element to excess actinic radiation in order to attempt to erase the remaining potential. The values of the potential remaining on the element after the initial cycle and after a plurality of such cycles of operation are measured, and the difference between these two values is calculated and is referred to as the buildup or increase in unerasable residual potential. The lower the amount of increase in unerasable residual potential after a given number of cycles of operation, the better are the regeneration characteristics of the element, and the longer is the useful life of the reusable element.

EXAMPLE 1

An electrophotographic element of the invention was prepared as follows.

A conductive support was prepared by vacuum-depositing a thin conductive layer of nickel onto a 178 micrometer thickness of poly(ethylene terephthalate) film.

Selenium photoconductor was then evaporation-deposited on the nickel-coated side of the conductive support to form a charge-generation layer (CGL) of 0.4 micrometer thickness.

A coating solution for forming a charge-transport layer (CTL) was then prepared comprising 10 weight percent solids dissolved in dichloromethane. The solids comprised the electron-transport agent of Structure (I-A) prepared as in Preparation A above and a polymeric binder comprising a polyester formed from 4,4'-(2-norbornylidene)diphenol and terephthalic acid:azelaic acid (40:60 molar ratio). The weight ratio of electron-transport agent:polymeric binder was 40:60. The solution was then coated onto the CGL and dried to form the CTL on the CGL. The combined thickness of CGL and CTL was 10 micrometers.

The resultant electrophotographic element was then corona-charged to a uniform positive potential of 480 V.

Dark decay rate of the initial potential was determined to be 3 V/s.

The uniformly charged element was subjected to simulated imaging exposure by exposing it through the outer surface of the CTL to radiation having a peak intensity at a wavelength of 500 nanometers (nm) (to which the selenium charge-generation material is sensitive, in order to generate electron/hole pairs in the CGL) at a rate of 3 ergs of radiant energy per square centimeter of element surface per second (3 ergs/cm$^2$s). The amount of incident actinic radiant energy necessary to discharge a given percentage of the initial uniform potential on the element (i.e., the electrophotographic speed) was determined to be 10.5 ergs/cm$^2$ to discharge 50% of the initial potential and 21.8 ergs/cm$^2$ to discharge 80% of the initial potential.

Regeneration characteristics of the element were determined by repeating a sequence of uniform charging, simulated imaging exposure, and erasure with excess radiation, a number of times. The increase in unerasable residual potential on the element after 2000 of such cycles of operation was 7 volts.

EXAMPLE 2

An electrophotographic element of the invention was prepared in a manner similar to that of Example 1, except that: the weight ratio of electron-transport agent:polymeric binder in the CTL was 30:70; the thin metal layer of the conductive support was aluminum; the CGL comprised the charge-generation material, titanyl tetrafluorophthalocyanine (described more extensively in U.S. Pat. No. 4,701,396), dispersed in the same binder material as employed in the CTL; and the element was stored in darkness for about 12 days before any dark decay, speed, or regeneration tests were carried out.

The CGL was prepared by dispersing the charge-generation material in a solution of the binder in dichloromethane (the weight ratio of charge-generation material:binder being 2:1), ball milling the dispersion for 60 hours, diluting with more dichloromethane to achieve suitable coating viscosity, coating the dispersion onto the conductive support, and drying off the solvent to yield a CGL of 0.5 micrometer thickness.

The electrophotographic element was corona-charged to a uniform positive potential of 483 V.

Dark decay rate of the initial potential was determined to be 14 V/s.

The uniformly charged element was subjected to simulated imaging exposure by exposing it through the outer surface of the CTL to radiation having a peak intensity at a wavelength of 820 nm (to which the charge-generation material is sensitive, in order to generate electron/hole pairs in the CGL) at a rate of 3.3 ergs/cm$^2$s. The amount of incident actinic radiant energy necessary to discharge 50% of the initial potential was 4.4 ergs/cm$^2$. To discharge 80% of the initial potential, required 13.6 ergs/cm$^2$.

Regeneration characteristics of the element were determined by repeating a sequence of uniform charging, simulated imaging exposure, and erasure with excess radiation, a number of times. The increase in unerasable residual potential on the element after 200 of such cycles of operation was 4 V.

EXAMPLE 3

An electrophotographic element of the invention was prepared as in Example 1, except that the electron-transport agent in the CTL was the compound of Structure (I-B) prepared as in Preparation B above.

The electrophotographic element was corona-charged to a uniform positive potential of 290 V.

Dark decay rate of the initial potential was determined to be 3 V/s.

Electrophotographic speed of the element was determined as in Example 1. The amount of incident actinic radiant energy necessary to discharge 50% of the initial potential was 9.6 ergs/cm$^2$. To discharge 80% of the initial potential, required 19.7 ergs/cm$^2$.

EXAMPLE 4

An electrophotographic element of the invention was prepared as in Example 2, except that the electron-transport agent in the CTL was the compound of Structure (I-B) prepared as in Preparation B above, and the weight ratio of electron-transport agent:polymeric binder in the CTL was 40:60.

The electrophotographic element was corona-charged to a uniform positive potential of 268 V.

Dark decay rate of the initial potential was determined to be 18 V/s.

Electrophotographic speed of the element was determined as in Example 2. The amount of incident actinic radiant energy necessary to discharge 50% of the initial potential was 4.2 ergs/cm$^2$, and 10.4 ergs/cm$^2$ were required in order to discharge 80% of the initial potential.

EXAMPLE 5

An electrophotographic element of the invention was prepared as in Example 1, except that the electron-transport agent in the CTL was the compound of Structure (I-C) prepared as in Preparation C above, and the weight ratio of electron-transport agent:polymeric binder in the CTL was 30:70.

The element was corona-charged to a uniform positive potential of 518 V.

Dark decay rate of the initial potential was determined to be 1 V/s.

Electrophotographic speed of the element was determined as in Example 1. The amount of incident actinic radiant energy necessary to discharge 50% of the initial potential was 13.2 ergs/cm$^2$, and 30.1 ergs/cm$^2$ were required in order to discharge 80% of the initial potential.

Regeneration characteristics were determined as in Example 1. The increase in unerasable residual potential on the element after 200 cycles of operation was 2 V.

EXAMPLE 6

An electrophotographic element of the invention was prepared as in Example 5, except that the polymeric binder in the CTL was bisphenol A polycarbonate sold under the trademark, Makrolon 5705, by Mobay Chemical Co., USA.

The element was corona-charged to a uniform positive potential of 496 V.

Dark decay rate of the initial potential was 1 V/s.

Electrophotographic speed of the element was determined as in Example 1. The amount of incident actinic radiant energy necessary to discharge 50% of the initial potential was 18.2 ergs/cm$^2$.

EXAMPLE 7

An electrophotographic element of the invention was prepared as in Example 2, except that the electron-transport agent in the CTL was the compound of Structure (I-C) prepared as in Preparation C above.

The element was corona-charged to a uniform positive potential of 422 V.

Dark decay rate of the initial potential was determined to be 33 V/s.

Electrophotographic speed of the element was determined as in Example 2, except that the simulated imaging exposure was at a rate of 3.09 ergs/cm$^2$s. The amount of incident actinic radiant energy necessary to discharge 50% of the initial potential was 5.9 ergs/cm$^2$, and 19.5 ergs/cm$^2$ were required in order to discharge 80% of the initial potential.

Regeneration characteristics were determined as in Example 2. The increase in unerasable residual potential on the element after 200 cycles of operation was 6 V.

EXAMPLES 8–10

An electrophotographic element of the invention (Example 8) was prepared as in Example 2, except that the electron-transport agent in the CTL was the compound of Structure (I-D) prepared as in Preparation D above. Two other elements of the invention, Examples 9 and 10, were prepared as in Example 8, except that the weight ratios of electron-transport agent:polymeric binder in the CTL's were 35:65 and 40:60, respectively.

The elements were corona-charged to uniform positive potentials of 454 V for Example 8, 434 V for Example 9, and 432 V for Example 10.

Dark decay rates of the initial potentials were determined to be 22 V/s for Example 8, 25 V/s for Example 9, and 26 V/s for Example 10.

Electrophotographic speeds of the elements were determined as in Example 2 except that the simulated imaging exposures were to radiation having a peak intensity at a wavelength of 800 nm at a rate of 3 ergs/cm$^2$s. The amounts of incident actinic radiant energy necessary to discharge 50% of the initial potentials were 12.6 ergs/cm$^2$ for Example 8, 11.1 ergs/cm$^2$ for Example 9, and 10.8 ergs/cm$^2$ for Example 10.

The invention has been described in detail with particular reference to certain preferred embodiments thereof, but it should be appreciated that variations and modifications can be effected within the spirit and scope of the invention.

What is claimed is:

1. In an electrophotographic element containing an electron-transport agent, the improvement wherein the electron-transport agent comprises a chemical compound having the structure

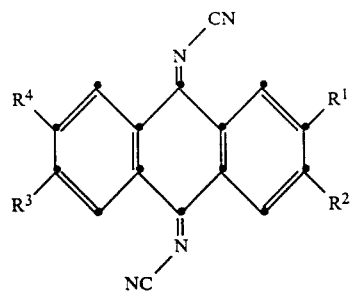

wherein:
one of R$^1$, R$^2$, R$^3$, and R$^4$ is acyclic alkyl having 2 to 10 carbon atoms or —COOR$^5$;

another one of $R^1$, $R^2$, $R^3$, and $R^4$ is H, acyclic alkyl having 1 to 10 carbon atoms, or $-COOR^5$;
the remaining two of $R^1$, $R^2$, $R^3$, and $R^4$ are each H; and $R^5$ is alkyl having 1 to 10 carbon atoms.

2. The electrophotographic element of claim 1, wherein $R^1$ is t-butyl, and $R^2$, $R^3$, and $R^4$ are each H.

3. The electrophotographic element of claim 1, wherein the element is a multiactive element comprising: an electrically conductive layer; a charge-generation layer comprising a photoconductive material; and a charge-transport layer comprising a polymeric film containing the electron-transport agent of claim 1.

* * * * *